United States Patent [19]

King, Jr.

[11] Patent Number: 5,705,696
[45] Date of Patent: Jan. 6, 1998

[54] EXTRACTIVE METHOD FOR THE PREPARATION OF QUATERNARY SALTS

[75] Inventor: Joseph Anthony King, Jr., Schenectady, N.Y.

[73] Assignee: General Electric Company, Schenectady, N.Y.

[21] Appl. No.: 691,168

[22] Filed: Aug. 1, 1996

[51] Int. Cl.$^6$ .................. C07C 209/68; C07D 233/58; C07F 9/02
[52] U.S. Cl. .................. 564/296; 564/291; 568/9; 548/335.1
[58] Field of Search .................. 564/291, 296; 568/9; 548/335.1

[56] References Cited

U.S. PATENT DOCUMENTS 4,487,698  12/1984  Idel et al. .................. 210/639
4,892,944  1/1990  Mori et al. .................. 544/107

FOREIGN PATENT DOCUMENTS 5178798  7/1993  Japan .................. 564/296
735631  8/1955  United Kingdom .................. 564/296

OTHER PUBLICATIONS

U.S. patent application Ser. No. 08/608,073, filed Feb. 28, 1996.

*Primary Examiner*—Peter O'Sullivan
*Attorney, Agent, or Firm*—William H. Pittman

[57] ABSTRACT

Quaternary (e.g., tetraalkylammonium and tetraalkylphosphonium) salts containing non-halide anions are prepared by performing an anion exchange reaction by liquid-liquid extraction with a chlorinated solvent of a mixture of an aqueous solution an alkali metal salt of the anion and a corresponding quaternary halide.

12 Claims, No Drawings

EXTRACTIVE METHOD FOR THE PREPARATION OF QUATERNARY SALTS

BACKGROUND OF THE INVENTION

This invention relates to the preparation of electrolyte compositions, and more particularly their preparation by an improved and inexpensive method.

Non-aqueous electrolytes are used in a number of applications including electrochemical cells and ultracapacitors. In particular, ultracapacitors have been proposed for use as replacements for batteries in electric vehicles and in vehicles with hybrid power sources. They have also been proposed as backup power sources to be used in case of power failures. Thus, the development of relatively cheap and effective electrolyte systems for ultracapacitors is of current interest.

The electrical behavior of an ultracapacitor depends on the formation of compact electrical double layers. In the typical construction of an ultracapacitor cell, two metallic current collectors are separated by porous electrodes, typically of carbon, which in turn are separated by a porous, non-conducting separator layer. The pores in the electrodes and separator are filled with an electrolyte.

In operation, a current is applied to the electrodes at a voltage below that at which an electrolytic reaction will take place. As a result, charged ions, typically from dissociation of salts in the electrolyte, accumulate on the surfaces of the electrodes, creating a potential difference which is available to produce current when desired.

A major challenge in ultracapacitor design is the selection of a suitable electrolyte. It might be expected that aqueous electrolytes would be preferred by reason of their very low cost. However, they are characterized by a low "potential window" by reason of the electrolysis of water at potentials above about 1.2 V. The potential windows of many organic systems are much higher, frequently on the order of 2.3–3.5 V, and therefore organic systems are under particular study.

A promising genus of electrolytes from the viewpoint of operativity employs nitrogen- or phosphorus-containing onium salts, illustrated by tetraethylammonium fluoborate, as electrolyte materials. These salts are generally dissolved in a solvent with high solvating power, good oxidation-reduction stability and low volatility, such as 1,2-propylene carbonate. The conductivities and potential windows of the fluoborates (i.e., tetrafluoroborates) and hexafluorophosphates are particularly advantageous.

One of the above-described quaternary ammonium salts, tetraethylammonium fluoroborate, is commercially available. However, it is extremely expensive because of the difficulty of its synthesis, which requires a first step of reaction of triethylamine with ethyl bromide in aqueous medium to form tetraethylammonium bromide, a second step of addition of sodium fluoroborate and membrane dialysis to remove by-product sodium bromide, and a final step of drying, as by freeze-drying or azeotropic distillation using a co-solvent. Depending on the concentration and purity desired, it may be necessary to employ more than one dialysis step.

It is of interest, therefore, to develop an improved method for preparing such quaternary salts which is easily and inexpensively carried out.

SUMMARY OF THE INVENTION

The invention is a method for preparing a quaternary ammonium or phosphonium salt having a non-halide anion which comprises intimately contacting an aqueous solution comprising a corresponding quaternary ammonium halide and an alkali metal salt of said anion with an organic liquid which is immiscible with said aqueous solution and which is a solvent for said quaternary salt, whereupon said quaternary salt is formed and transferred to said organic liquid.

DETAILED DESCRIPTION; PREFERRED EMBODIMENTS

The quaternary salts which may be prepared according to the present invention include such salts as the tetraalkylammonium and tetraakylphosphonium salts in which the alkyl groups contain about 1–10 and especially about 1–6 carbon atoms and N-alkylimidazolium salts. The anions in said salts are other than halides and include such anions as fluoborate, hexafluorophosphate, sulfate, perchlorate, hexafluoroantimonate, hexafluoroaluminate, hexafluoroarsenate, hexafluorosilicate, hexafluorostannate, hexafluorotitanate, hexafluorogermanate, trifluoromethylsulfonate, and $(CF_3SO_2)_2N^-$.

Particularly advantageous as electrolytes are the salts in which the anion has the formula $ZF^-_m$, wherein Z is an element capable of forming a perfluorinated anion; and m−1 is the valence of Z. Especially preferred are the fluoborate and hexafluorophosphate salts.

In the liquid-liquid extraction method of this invention, the quaternary halide undergoes reaction with an alkali metal, most often sodium, salt having the desired artion. The quaternary halide and alkali metal salt are typically introduced in aqueous solution, frequently the same aqueous solution, and are contacted batchwise or continuously with a water-immiscible organic liquid which is capable of dissolving the product quaternary salt. Chlorinated alkanes, especially methylene chloride, are often preferred for this purpose. The molar ratio of alkali metal salt to quaternary halide is at least about 1.0:1 and preferably about 2.2–5.0:1.

Upon contact of the immiscible liquid with the aqueous solution, an exchange reaction takes place which is driven by the tendency of the quaternary salt to migrate to the organic phase, while by-product alkali metal halide remains in the aqueous phase. Contact between the aqueous and organic phases for this purpose is typically at temperatures in the range of about 20°–100° C., most often about 20°–30° C. Again, the reaction can often be conducted to produce essentially quantitative yields of the desired product.

Following preparation, the quaternary salt may be isolated and purified by conventional methods. It is often highly preferred to dry the solution of product over a drying agent such as sodium sulfate, magnesium sulfate or molecular sieves. Solvents may then be removed by evaporation, and purification effected by recrystallization from an organic liquid or mixture of organic liquids. The identities of suitable liquids will be apparent to those skilled in the art or can be determined by simple experimentation. Often, a mixture of one liquid in which the product is highly soluble and another in which it has low solubility is employed. Mixtures comprising such liquids as toluene, chlorobenzene, o-dichlorobenzene, ethyl acetate, methylene chloride, chloroform and ethyl ether in varying proportions may conveniently be employed.

The method of this invention is illustrated by the following examples.

EXAMPLE 1

A 1000-ml round-bottomed flask equipped with a magnetic stirrer was charged with 600 ml of methylene chloride.

A 1-l heavier-than-water liquid-liquid extractor, equipped with a reflux condenser, was attached and charged with about 150 ml of methylene chloride, enough to cover the side siphon port. A solution of 60 g (546.4 mmol) of sodium fluoborate and 45.94 g (218.6 mmol) of tetraethylammonium bromide in 600 ml of deionized water was layered onto the methylene chloride phase in the extractor. The flask was immersed in a heat bath at 60° C. and the methylene chloride was heated under reflux for 18 hours. The organic phase was then removed, dried over magnesium sulfate and vacuum stripped. The product, in the form of small prismatic crystals, was dried overnight at 50° C. under vacuum. It was found by analysis to be the desired tetraethylammonium fluoborate, obtained in quantitative yield and having no residual bromide detectable by capillary electrophoresis.

EXAMPLES 2–8

The procedure of Example 1 was repeated, using the quaternary salts and alkali metal salts listed in the following table. In each example, a quantitative yield of product having no detectable fluoride, chloride or bromide was obtained.

| Example | Quaternary salt | Alkali metal salt |
|---|---|---|
| 2 | Tetraethylammonium chloride | $NaBF_4$ |
| 3 | Tetraethylammonium bromide | $NaPF_6$ |
| 4 | Tetramethylammonum chloride | $NaBF_4$ |
| 5 | Tetra-n-butylammonium chloride | $NaBF_4$ |
| 6 | Tetra-n-butylphosphonium bromide | $NaBF_4$ |
| 7 | Tetra-n-butylphosphonium chloride | $NaBF_4$ |
| 8 | Tetraethylphosphonium bromide | $NaBF_4$ |

What is claimed is:

1. A method for preparing a quaternary ammonium or phosphonium salt having an anion of the formula $ZF^-{}_m$ wherein Z is an element capable of forming a perfluorinated anion and m-1 is the valence of Z, which comprises intimately contacting an aqueous solution comprising a corresponding quaternary ammonium halide and an alkali metal salt of said anion with an organic liquid which is immiscible with said aqueous solution and which is a solvent for said quaternary salt, whereupon said quaternary salt is formed and transferred to said organic liquid.

2. A method according to claim 1 wherein the organic liquid is a chlorinated alkane.

3. A method according to claim 2 wherein the chlorinated alkane is methylene chloride or chloroform.

4. A method according to claim 3 wherein the chlorinated alkane is methylene chloride.

5. A method according to claim 1 wherein Z is boron and m is 4.

6. A method according to claim 1 wherein Z is phosphorus and m is 6.

7. A method according to claim 1 wherein the salt prepared is a tetraalkylammonium salt.

8. A method according to claim 7 wherein the alkyl groups contain about 1–6 carbon atoms.

9. A method according to claim 8 wherein the alkyl groups are methyl, ethyl or n-butyl groups.

10. A method according to claim 1 wherein the salt prepared is a tetraalkylphosphonium salt.

11. A method according to claim 10 wherein the alkyl groups contain about 1–6 carbon atoms.

12. A method according to claim 11 wherein the alkyl groups are ethyl or n-butyl groups.

* * * * *